United States Patent [19]

Orthwein

[11] 4,060,898
[45] Dec. 6, 1977

[54] CLIP-ON DENTAL RESTORATION AND TOOLS FOR REMOVING SAME

[76] Inventor: William C. Orthwein, P.O. Box 3332, Carbondale, Ill. 62901

[21] Appl. No.: 692,759

[22] Filed: June 4, 1976

Related U.S. Application Data

[62] Division of Ser. No. 613,196, Sept. 15, 1975, abandoned.

[51] Int. Cl.$^2$ ............................................. A61C 13/12
[52] U.S. Cl. .................................................. 32/40 R
[58] Field of Search ................... 32/66, 40 R; 81/419, 81/418, 425 A, 426, 5.1 R, 415; 30/271

[56] References Cited

U.S. PATENT DOCUMENTS

| | | | |
|---|---|---|---|
| 960,963 | 6/1910 | Kyle | 30/271 |
| 2,989,099 | 6/1961 | Damm | 81/418 |

Primary Examiner—Robert Peshock
Attorney, Agent, or Firm—Donald D. Jeffery

[57] ABSTRACT

The invention relates to a removable dental restoration for filling an edentulous space defined at each end by a natural tooth, the restoration having at each end a means for resiliently gripping the adjacent natural tooth. In a first embodiment, the gripping means is releasable by application of opposing forces to the longitudinal side walls of the restoration. A second embodiment has the gripping means releasable by applying a simultaneous force to the end wall of each respective gripping means. A plier-type tool is provided for removing the first type of restoration, wherein the plier jaws have a rigid convex central portion surrounded by resiliently compressible locating fingers. The locating fingers permit the jaws to be located at the proper position on the restoration at which time closing of the jaws causes the convex central portions of the jaws to press against the longitudinal walls of the restoration, thereby releasing the gripping means. A tool is provided for removing the second type of restoration by applying forces to simultaneously release the gripping means at each end of the restoration.

2 Claims, 14 Drawing Figures

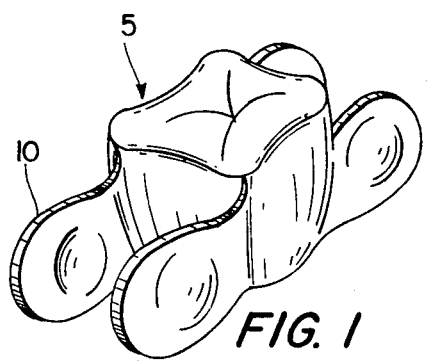
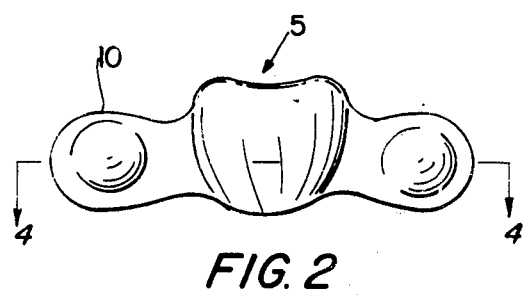
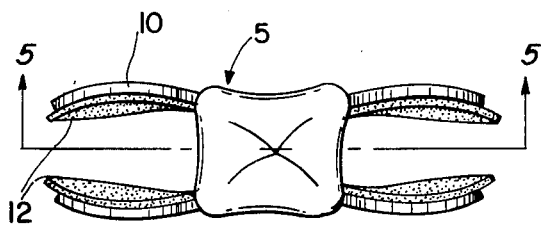
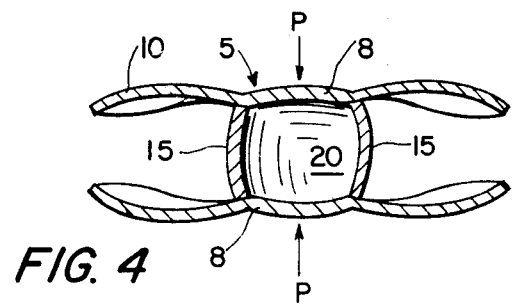
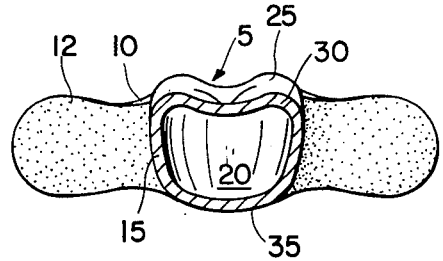
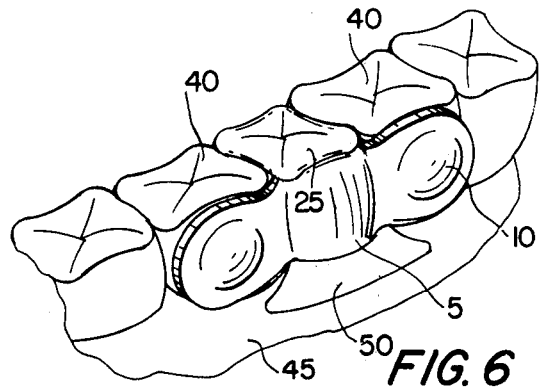
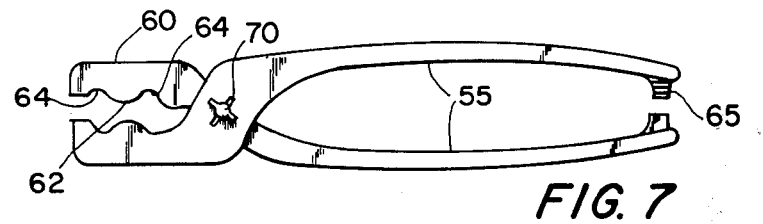
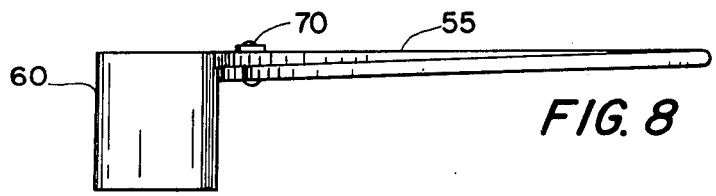

CLIP-ON DENTAL RESTORATION AND TOOLS FOR REMOVING SAME

This is a division of application Ser. No. 613,196, filed Sept. 15, 1975, and now abandoned.

BACKGROUND OF THE INVENTION

The Prior Art

Many types of restorations are known in the art which employ clamps, clasps, and the like for gripping adjacent teeth by the temporary bridge tooth. However, the clamp is ordinarily cemented or otherwise fastened to the side of the false tooth and therefore is not easily releasable. For example, U.S. Pat. No. 3,047,952 discloses a clasp for removable false teeth which is only partially embedded in the false tooth. While this type of clasp does effectively hold the restoration in place for most purposes, it may not have sufficient gripping force to hold the restoration during vigorous mastication of chewy or tough foods. Should the clasp be made with sufficient gripping forces to hold the restoration in place during such mastication, it may be difficult to remove for cleaning and would not be easily replaced.

Other types of removable bridges are also known in which the gripping means are releasable by moving a lever which protrudes from the outside surface of the restoration. For example, French Pat. No. 780,623 discloses a bridge which is split vertically so that it may be removed by sliding a release lever. This type of restoration has the disadvantage of moving parts and blind holes which may break down or collect foreign particles. The restoration may be difficult to keep clean.

U.S. Pat. No. 2,722,052 shows the use of a metallic base having clasps for gripping the adjacent teeth and having openings for receiving porcelain or other artificial teeth. This type of restoration may have some of the drawbacks associated with the restoration disclosed in U.S. Pat. No. 2,047,952, as discussed above.

There is a clear need in the art for a dental restoration which will firmly grasp the natural teeth adjacent to an edentulous space in the mouth, yet be easily releasable for removal and cleaning without having blind holes or moving parts to break down or collect food particles.

SUMMARY OF THE INVENTION

The present invention comprises a removable dental restoration for filling an edentulous space in the mouth defined at each side by a natural tooth. The restoration has releasable gripping means for engaging the adjacent natural teeth. In a first embodiment, a single restoration is provided and the gripping means is releasable by applying side pressure to the resilient longitudinal walls of the restoration. A plier-like tool is provided for applying such pressure at the proper location. A second embodiment of the present invention includes a series of restorations and has the gripping means releasable by applying pressure to a single wall of the gripping means at each end of the restoration. A tool is also provided for application of pressure at the correct points for removal of the latter type of restoration.

The principal objective of the present invention is to provide a removable dental restoration which may comprise a single restoration or a series of restorations and which, in either form, are firmly and resiliently clamped in place and which can be quickly and easily removed for cleaning purposes.

BRIEF DESCRIPTION OF THE APPLICATION DRAWINGS

FIG. 1 is a perspective view of a first embodiment of the present invention;

FIG. 2 is a front elevational view of the restoration of FIG. 1;

FIG. 3 is a top plan view of the restoration of FIGS. 1 and 2;

FIG. 4 is a cross-sectional view taken along line 4—4 of FIG. 2;

FIG. 5 is a cross-sectional view taken along line 5—5 of FIG. 3;

FIG. 6 illustrates the dental restoration of FIG. 1 with an attached base portion and shown in position between the natural teeth which define an edentulous space;

FIG. 7 is a top plan view of a tool for releasing the gripping means of the restoration of FIGS. 1-6;

FIG. 8 is a front elevational view of the tool of FIGS. 7 and 8 with locating fingers in place and engaging the longitudinal wall of the dental restoration;

DETAILED DESCRIPTION OF THE PREFERRED EMBODIMENTS

Figure 9:
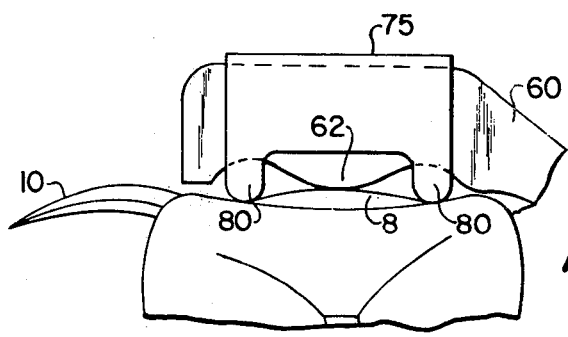
FIG. 9 is a view of the tool of FIGS. 7 and 8 having a resiliently compressible glove over the jaw face.
Figure 10:
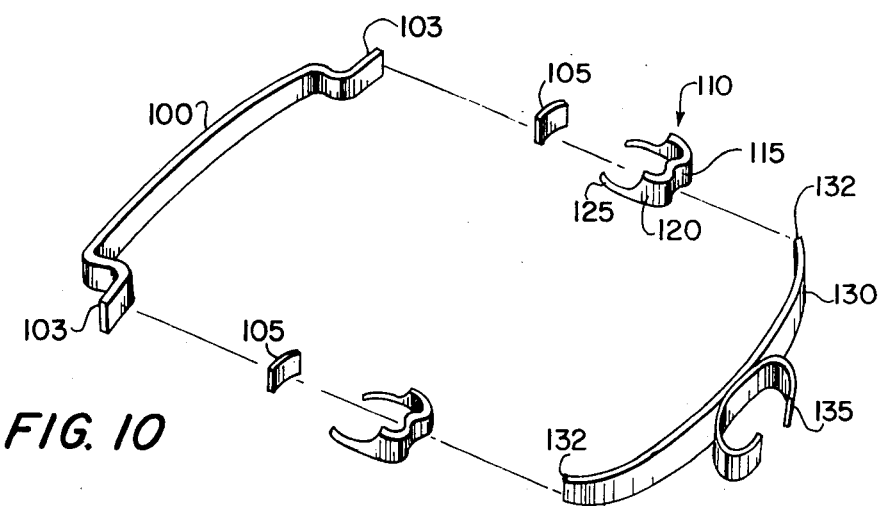
FIG. 10 is an exploded view of a second embodiment of the present invention.

Referring initially to the form of the invention illustrated in FIGS. 1-9 of the drawings. FIG. 1 is a perspective view of the dental restoration, which includes a central body portion 5 shaped to simulate a natural tooth and gripping means 10 at each end for at least partially encircling and grasping natural teeth at both sides of the restoration. As can be seen in FIGS. 2 and 3, the gripping means are formed to complement the contour of the adjacent teeth to be gripped in order to provide a more secure fastening of the restoration in the mouth. As shown in FIG. 4, longitudinal walls 8 and end walls 15 form the central body portion of the restoration which has a hollow central area 20. The gripping means comprise gripping arms 10 at each end of the body portion which are preferably integrally formed with the longitudinal walls 8. The longitudinal walls and gripping arms are formed from a resilient material, such as spring metal, and the end walls 15 can likewise be formed of metal and are relatively rigid so as to provide the desired firmness or rigidity to the restoration. The end walls 15 may be separately formed as shown in FIG. 4 and secured to the longitudinal walls 8 to form the body portion.

To install the restoration, inwardly directed pressure is applied to the longitudinal walls 8 of the body portion, which causes the walls to flex inwardly and, because of the fulcrum effect of the rigid end walls 15, the gripping arms 10 are caused to spread apart. Releasing the pressure against the resilient, longitudinal walls 8 will permit the longitudinal walls to flex outwardly to their original position, thus causing the gripping arms 10 to close. Cushions of nylon, or other relatively soft material, may optionally be inserted between the gripping arms and the natural teeth being gripped so that the holding forces may be uniformly distributed over the natural teeth. This cushion material should be inert relative to the chemicals in the mouth and the foods eaten. Such a cushion material is shown attached to the gripping surfaces of gripping arms 10 at the left portion of FIG. 3.

Referring to FIG. 5, the central body portion of the restoration further includes lower and upper walls 30 and 35, respectively, which, along with longitudinal walls 8 and end walls 15, define the hollow central area 20. In FIG. 5, the central body portion is shown having a crown 25 superimposed on the upper wall 35 to simulate a natural tooth. This crown may be of porcelain, acrylic or other materials known in the art. The central body portion and gripping means are preferably constructed of relativvely inert metals, such as stainless steel and gold, although it is to be understood that synthetic materials could also be employed if they possess the necessary characteristics. While the restoration of FIGS. 1-9 is shown with a central body portion having substantially flat walls, it is to be noted that the walls may be curved so that the central body portion defines a cylindrical, triaxial ellipsoidal, prolate spheroidal, oblate spheroidal or spherical form.

In FIG. 6, the restoration is shown in place in an edentulous space in the mouth defined by adjacent natural teeth commonly indicated at 40 and natural gum 45. The restoration is provided with a base 50, preferably of flesh-colored material such as acrylic. The base is cast to fit the contour of the gum and ridge of the edentulous space and serves to provide support and lend a more pleasing appearance. Further support for the restoration may be obtained from brackets resting on the adjacent teeth.

Although the longitudinal walls may be constructed of weak enough spring material that the restoration may be removed by finger forces, it is preferable to have more gripping force than such springs would provide. A tool for removing the dental restoration of FIGS. 1-6 is accordingly shown in FIGS. 7 and 8. The tool generally resembles a pliers and includes a pair of handles 55 which are pivotally interconnected by a pin 70. The pin 70 is formed integrally with one of the handles 55. Each handle has at the gripped end a small stop 65, the stops being in opposing positions on the handles so that full closure of the jaws is not permitted. In addition, pin 70 is keyed so that the jaw handles may be separated for cleaning. Each handle is formed at its opposite end with a gripping jaw 60 shaped to include a rigid central convex portion 62 defined by adjacent channels 64. In FIG. 9 the jaw face shown is provided with a resiliently compressible glove 75 having locating fingers 80 extending into the channels 64. The locating fingers so extend beyond the apex of the convex central portion 62 of the jaw face that when the jaws are arranged around a restoration as shown in FIG. 9, the locating fingers will aid in positioning the jaw faces so that the convex portions 62 of the jaws will contact the central body portion of the restoration at the mid point of the longitudinal walls 8. Closing the jaws slightly will flex the longitudinal walls inwardly; thereby releasing the gripping arms 10, as above described. Stops 65 are provided to prevent excess pressure on the longitudinal walls. The pliers may be of any conventional rigid material such as metal or a rigid synthetic material, while the glove and locating fingers are preferably constructed from a soft plastic material.

The dental restoration of the first embodiment may have the central body portion shaped to simulate a natural tooth or may be made smaller than the edentulous space to be filled and embedded in a material which simulates a natural tooth. As noted above, a crown 25 may be fastened to the upper wall 35 of the central body portion. A flexible coating such as nylon might also be applied to the gripping means and longitudinal walls to simulate the natural tooth coloring.

Figure 11:
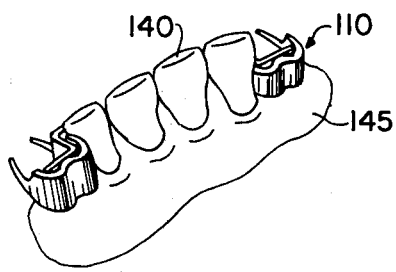
FIG. 11 shows the restoration of FIG. 11 assembled and having a lower base portion.
Figure 12:
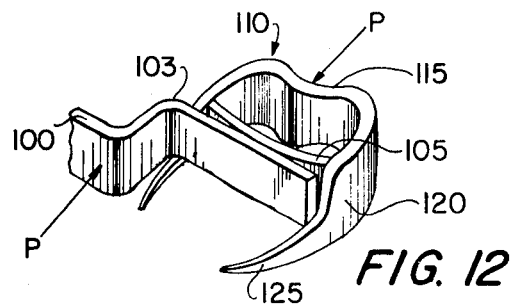
FIG. 12 is a detailed showing of the spring segment and gripping means of the embodiment of FIG. 10.
Figure 13:
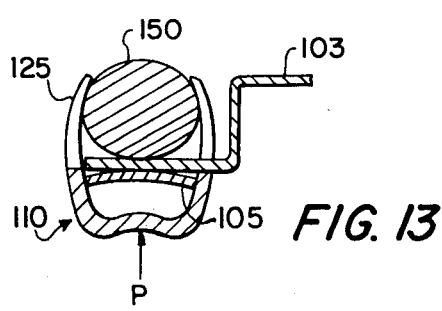
FIGS. 13 and 14 illustrate how the embodiment of FIG. 10 grips an adjacent natural tooth.
Figure 14:
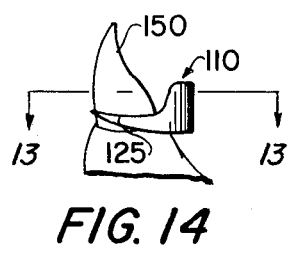

Reference is now made to the form of the invention illustrated in FIGS. 10-14. The restoration in this form is designed to fill an edentulous space having a length equal to several missing teeth, with the space being defined at each side by a natural tooth and having a ridge along the gum. A rigid bar 100 is shaped to follow the curve of the natural ridge and has offset sections 103 at each end which extend partially around the natural tooth to be gripped. Spring segments 105 are fastened to the offset sections 103 as shown in FIG. 12 by soldering or other means. A gripping means 110 is provided at each end of the restoration for engaging the spring segment 105 and the adjacent tooth to be gripped. Each gripping means is generally U-shaped and has an end wall 115, side walls 120 extending perpendicularly to the end wall and spaced apart for engaging the spring segment, and prongs 125 extending from each side wall for gripping the natural tooth. Side walls 120 of the gripping means 110 are slanted sufficiently so that when spring segment 105 is pressed toward end wall 115, the side walls will spread apart, releasing the gripping effect of prongs 125. The prongs 125 are small enough to fit the spaces between natural teeth at the gum line. Application of directional forces P to the ends of restoration, as shown in FIG. 12 at one end of the restoration, will cause the prongs 125 to disengage a natural tooth 150 being gripped, as shown in FIG. 13.

The rigid bar 100 supports a series of artificial teeth 140, as shown in FIG. 11, with the bar being preferably embedded in the artificial teeth. A base portion 145 cast to fit the contour of the gum simulates the natural gum and provides vertical support for the restoration. The artificial teeth 140 and base portion 145 may be of any suitable material, such as acrylic.

A special tool is provided for applying the appropriate forces for removal of the restoration shown in FIG. 11 from the mouth of the wearer. The tool consists of a curved removal bar 130 having tips 132 protruding at an angle to the longitudinal axis of the bar and being spaced sufficiently apart for simultaneously contacting the end walls 115 of the gripping means 110, as can be seen from the exploded, FIG. 10 view. A finger clip 135 is provided so that the user may insert the index finger into the finger clip and apply the tool to the gripping means. By manually pressing the removal bar toward the rigid bar 110, the prongs 125 will be disengaged and the restoration may be easily lifted from the mouth for cleaning. It will be noted that the gripping means 110 protrudes inwardly into the mouth when the restoration is in place. However, such protrusion is not sufficient to cause discomfiture to the wearer.

It will be understood by those skilled in the art that various modifications of the present invention are possible without, however, departing from the spirit and scope of the present invention as defined by the appended claims.

I claim:

1. A tool for applying inward pressure to the longitudinal walls of a removable dental restoration comprising a pair of gripping handles, each of said handles having a jaw formed at one end thereof, the face of each jaw having a rigid central convex portion defined by adjacent channels and each said channel having located therein a resiliently compressible locating finger extending so that when said jaws are closed on said restoration, said fingers will compress until said convex portions contact said longitudinal walls.

2. The apparatus of claim 1, wherein said tool includes means on said handles for preventing said jaws from fully closing.

* * * * *